United States Patent [19]

Liu et al.

[11] Patent Number: 4,550,017

[45] Date of Patent: Oct. 29, 1985

[54] FLUORESCENCE SCREENING FOR BLOOD TYPING

[75] Inventors: Yen-Ping Liu, Santa Clara; Edwin F. Ullman, Atherton; Martin J. Becker, Palo Alto, all of Calif.

[73] Assignee: Syntex (U.S.A.) Inc., Pala Alto, Calif.

[21] Appl. No.: 434,761

[22] Filed: Oct. 15, 1982

[51] Int. Cl.⁴ .................. G01N 33/54; G01N 33/80
[52] U.S. Cl. ........................... 424/11; 436/520; 436/533; 436/534; 436/548; 436/827
[58] Field of Search ............... 424/11; 436/548, 533, 436/827, 546, 537, 520, 534

[56] References Cited

U.S. PATENT DOCUMENTS

| | | | |
|---|---|---|---|
| 4,035,316 | 7/1977 | Yen et al. | 436/827 |
| 4,193,983 | 3/1980 | Ullman | 436/537 |
| 4,219,335 | 8/1980 | Eberson | 436/808 |
| 4,261,968 | 4/1981 | Ullman | 436/537 |
| 4,275,053 | 6/1981 | Rosenfield et al. | 424/11 |

FOREIGN PATENT DOCUMENTS 2963 7/1979 European Pat. Off. .

OTHER PUBLICATIONS

Chemical Abstracts, 92:18399w, (1980).
Hudson et al., "*Practical Immunology*", 2nd ed., (1980), Blackwell Sc. Pub., Oxford, p. 139.
Smith, *FEBS Letters*, 1977, vol. 77, p. 25.

*Primary Examiner*—Sidney Marantz
*Attorney, Agent, or Firm*—Bertram I. Rowland; Theodore J. Leitereg

[57] ABSTRACT

A sensitive method for identifying red blood cell antigens or antibodies thereto is provided. A fluorescent bead is conjugated to a receptor specific for a red blood cell antigen (ligand) or alternatively with an antigen for determination of antibodies. The conjugate is mixed with a red blood cell containing composition. A change in fluorescence compared with a control reveals the presence or absence of the antigen or antibody.

8 Claims, No Drawings

FLUORESCENCE SCREENING FOR BLOOD TYPING

FIELD OF THE INVENTION

The mammalian red blood cells (RBC) carry numerous antigens some of which must be accurately identified in both patient and donor for medical procedures such as transfusions. Accurate detemination of blood groups, A, B, AB or O and determination of Rh factors can be critically important. Also antibodies present in the blood to such antigens can be of diagnostic interest.

Conventionally, agglutination techniques are used on a microscope slide or in a tube. Improved rapid accurate screening of red blood cells is desirable in view of the large numbers of samples which must be tested.

DESCRIPTION OF THE PRIOR ART

Identification of red blood cell (RBC) antigens by agglutination techniques is standard, e.g. C. Hudson and F. C. Hay, *Practical Immunology*, Second Edition, Blackwell Scientific Publications, Oxford, (1980), p. 139. U.S. Pat. No. 3,862,303 is exemplary of immunological detection and identification of serological factors using carrier particles such as latex beads. Smith, FEBS Letters 77,25 (1977) describes a fluroescent immunoassay.

SUMMARY OF THE INVENTION

A method is provided for typing red blood cells (RBC) or antibodies to the blood cells using fluorescent particles. The particles are conjugated to a homologous receptor which binds specifically to a predetermined RBC surface ligand or antigen. If the RBCs have the homologous ligand, binding occurs and the fluorescence is quenched. For detection of antibodies, RBCs having the appropriate antigen are used and in the presence of the antibodies, fluorescence is reduced.

DESCRIPTION OF THE SPECIFIC EMBODIMENTS

The subject invention provides a novel method for typing red blood cells or identifying red blood cell (RBC) antigens or the antibodies thereto by using the RBCs as fluorescence quenchers in an assay employing fluorescent particles to provide a detectable signal. Substances which bind to RBC antigens, normally antibodies or lectins (hereinafter "receptors") are conjugated to fluroescent particles. A solution of particle-conjugates is combined with red blood cells, e.g., whole blood, with an appropriate buffer. If an antigen is present on the RBC's that has a binding or determinant site specific for the receptor, the conjugated particles will bind to the RBCs which act as fluorescence quenchers.

The receptor which is employed binds preferentially to different RBC surface antigens. Thus there will be a fluorometrically measurable decrease when a given antigen is present as compared to when that antigen is absent in a given RBC sample. For example, in the A, B, O system, if the fluorescent particle were conjugated to anti-A antibody, binding would occur and there would be a greater decrease in fluorescence if the analyte contained the A antigen of type A or type AB blood than if the analyte contained blood types B or O.

In addition to antibodies, certain lectins are known to bind in varying degrees to RBC surface antigens, and are convenient receptors for use in fluorometric assays.

The subject method can also be used for determining the presence of antibodies to a RBC antigen. Two different techniques may be used. In one, antibody conjugated fluorescent particles compete with antibodies in the plasma or serum sample for antigen sites on RBCs of a known group, with the observed fluorescence increasing with increasing amounts of antibodies against the specific antigen in the sample. Alternatively, the fluorescent bead may be conjugated with the surface antigen of interest and antibodies present in the sample act as a bridge between RBCs of known type and the antigen conjugated fluorescent particles. In this situation, decreasing fluorescence would indicate the presence of the antibodies.

In choosing a fluorescer, since RBC's are optically dense at wavelengths of greather than 415 nm, either the fluorescence excitation or emission should desirably be measured at or above this wavelength, usually between about 400 to 430 nm.

High extinction coefficients for the fluorescer are desirable and should be greatly in excess of 10, and preferably in excess of 100. Fluorescent particles are chosen to have a high quantum yield.

In addition, it is desirable that the fluorescer have a large Stokes shift, preferably greater than 20 nm, more preferably greater than 30 nm. That is, it is preferred that there be a substantial spread or difference in wavelengths for the fluorescer between its absorption maximum and emission maximum.

One group of fluorescers having a number of the desirable properties are the xanthene dyes, which include the fluoresceins derived from 3,6-dihydroxy-9-phenylxanthhydrol and rosamines and rhodamines, derived from 3,6-diamino-9-phenylxanthene. The rhodamines and fluoresceins have a 9-0-carboxyphenyl group, and are derivatives of 9-0-carboxyphenylxanthene.

These compounds are commercially available with or without substituents on the phenyl group.

Another group of fluroescent compounds are the naphthylamines, having an amino group in the alpha or beta position, usually alpha position. Included among the naphthylamino compounds are 1-dimethylaminonaphthyl-5-sulfonate, 1-anilino-8-naphthaline sulfonate and 2-p-toluidinyl-6-naphthalene sulfonate. Other fluorescers of interest include coumarins, e.g., umbelliferone, and rare earth chelates, e.g., Tb, Eu, etc.

Appropriate particles, are combined with the fluorescer using standard techniques to provide fluorescent beads or microspheres. Fluorescent particles are commercially available. The fluorescent beads may be varied widely as to size and composition, they will generally be of a size in the range of about 0.1 to $2\mu$ in diameter, more usually about 0.6 to $1\mu$. The beads will normally be made of an inert material and include a plurality of fluorescent chromophoric functionalities. The beads will have a sufficient concentration of fluorescent functionalities to provide for a large signal per bead. Various organic polymers may be employed for the bead, e.g. polystyrene, polymethacrylate or the like or inorganic polymers, e.g. glass or combinations thereof. The particular choice of the polymeric composition is primarily one of convenience.

Conjugated to the fluorescent beads either covalently or non-covalently are receptors which may be antibodies, including monoclonal antibodies, or lectins, that bind either specifically or differentially to specific RBC surface antigens or antigens having the determinant site(s) of such RBC surface antigens.

The receptors are adsorbed to the fluorescent bead using standard techniques extensively described in the literature, which need not be repeated here. Alternatively, the receptors may be covalently bound by conventional techniques.

In carrying out the assay, an RBC sample in a buffered aqueous solution comprising from 1–50%, preferably about 2–20% more preferably about 3–5% RBC's by volume, is mixed with an approximately equal volume of the conjugated fluorescent bead - receptor solution having a concentration of fluorescent beads of from about 0.1 to 5, usually 0.1 to 3 weight percent.

As a control, an identical volume of fluorescent bead solution lacking the RBC-binding capacity may be mixed with an equal volume of RBC solution. The mixed solutions are allowed to stand for up to 120 min., preferably 1–10 minutes at mild temperatures from above 0° C. to about 37° C., preferably about 15°–25° C. Other controls may be used. Free antigen or antibody could be added as an example, or the result could be compared with standard preparations of Type A, B or O blood or serum.

The following examples are by way of illustration and not by way of limitation.

EXPERIMENTAL

I. Preparation of a fluorescent latex

In a test tube, a solution of 5.0 ml of 0.1% w/v Triton X-100 in phosphate-buffered saline (PBS) was combined with 0.035 ml of a 0.2 M solution of a dye (Coumarin 153, Eastman Kodak) in troluene. After thorough mixing, there resulted a somewhat opalescent solution. To this dye/detergent mixture was added 0.50 ml of a 2.5% suspension of a monodisperse polystyrene latex of 0.5μ particle size (Polysciences). This mixture was stored for 3 hrs, then centrifuged and washed thoroughly with 0.1% Triton X-100 in PBS. The latex suspension was then made up to 5.0 ml in 0.1% Triton X-100 in PBS.

II. Adsorption of *Ulex europaeus* lectin to fluorescent latex

150 μl of the above dyed latex, 2.5% in PBS/TX-100, was added to 1.0 ml glycine-buffered saline (GBS), pH 8.2. To the latex suspension was added 200 μl of a 2.0 mg/ml solution of *U. europaeus* lectin (Sigma). The suspension was mixed thoroughly and centrifuged. The supernatant was discarded. The latex was resuspended in GBS, and again treated with 200 μl of a 1.0 mg/ml solution of *U.e.* lectin in GBS. The suspension was mixed thoroughly and then centrifuged. The supernatant was discarded. The latex was resuspended in 1.0 ml GBS and treated with a third 0.20 ml portion of 1.0 mg/ml *U.e.* lectin in GBS. The suspension was mixed thoroughly and incubated at 37° C. for 2 hr. The latex was then centrifuged out and washed twice with 1 mg/ml rabbit serum albumin in GBS. The latex was then suspended in 100 μl RSA/GBS.

A second portion of dyed latex was treated as above, except that rabbit serum albumin (RSA) was substituted for the lectin. This material served as a control for testing of the latexes.

III. Demonstration of "quenching" of fluorescent latex on binding to a RBC

The latex, either lectin-conjugated or RSA control, was tested at either 1:10 dilution or neat.

Protocol: 10 μl latex suspension was mixed with 10 μl of a 3% suspension of RBS's (Dade). RBC's used were type B or type O. After 3 min at room temperature, 1.0 ml RSA/GBS was added. The fluorescence intensity was measured with excitation at 415 nm and emission monitored at 490 nm.

The results are as follows:

| Tube # | Latex, | dilution | Red cell type | Reading |
|---|---|---|---|---|
| 1 | U.e., | neat | B | 117 |
| 2 | " | " | O | 95 |
| 3 | " | " | No RBC | 234 |
| 4 | RSA control, | " | B | 148 |
| 5 | " | " | O | 149 |
| 6 | " | " | No RBC | 243 |
| 7 | U.e., | 1:10 | B | 18.4 |
| 8 | " | " | O | 14.4 |
| 9 | " | " | No RBC | 34.0 |
| 10 | RSA control, | 1:10 | B | 20.5 |
| 11 | " | " | O | 20.7 |
| 12 | " | " | No RBC | 32.4 |
| 13 | Buffer blank | | | 1.4 |

The following is concluded:
A. The presence of RBC's nonspecifically reduced the fluorescence intensity to ca. 61% of the base value.
B. The neat latex had its fluorescence reduced to 78% of control by type B RBC's, 63% of control by type O RBC's. For 1:10 dilution, the reduction was to 89% of control by type B; 57% of control by type O.
C. The results between B and O are in accord with the known specificity of *U.e.* lectin, which is a strong agglutinator of O and weak for A and B. Similarly, the apparent specificity of O over B increases with dilution.
D. Reproducibility of the results for the controls is good. Compare tubes 3 and 6; 9 and 12. Also compare tubes 4 and 5; 10 and 11.

The subject invention provides a novel method for identifying red blood cell antigens. Because of the high opacity of an RBC solution, it was not obvious that one could fluorometrically measure change in fluorescence in such a solution, nor that the red blood cells would act as an efficient reliable fluorescence quencher. The subject method is rapid, simple and accurate and is useful for research and clinically, especially in situations where large numbers of blood samples have to be typed quickly and accurately, e.g. blood banks.

Although the foregoing invention has been described in some detail by way of illustration and example for purposes of clarity and understanding, it will be obvious that certain changes and modificatons may be practiced within the scope of the appended claims.

What is claimed is:
1. A method for determining in a sample the presence of a surface antigen of red blood cells bound to said cells or antibodies to such surface antigen, which comprises:
   combining a sample suspected of containing either a surface antigen of red blood cells bound to said cells or antibodies to said surface antigen with fluorescent particles conjugated with either (1) receptor homolgous to said surface antigen ("receptor conjugate") or (2) said surface antigen ("antigen conjugate");
   wherein for the determination of the surface antigen bound to said red blood cells only receptor conjugate is employed, and
   for the determination of said antibodies: (a) antigen conjugate is employed in combination with red blood cells having the same antigen or (b) receptor conjugate is employed in the presence of red blood cells having an homologous surface antigen; and determining the change in fluorescence as compared to a sample having a known red blood cell antigen or antibody thereto.

2. A method according to claim 1 wherein said surface antigen is selected from the group consisting of A antigen and B antigen.

3. A method according to claim 1, wherein said surface antigen is Rh factor.

4. A method according to claim 1 wherein said receptor is an antibody to a red blood cell surface antigen.

5. A method according to claim 4 wherein said antibody is a monoclonal antibody.

6. A method according to claim 1 wherein said receptor is a lectin.

7. A method according to claim 1 wherein said fluorescent particle is a latex particle.

8. A method according to claim 1, wherein said receptor conjugate is employed for the detection of antibodies.

* * * * *